United States Patent
Van Raaij et al.

(10) Patent No.: US 6,740,511 B1
(45) Date of Patent: May 25, 2004

(54) MODIFIED ADENOVIRAL FIBRE AND USES THEREOF

(75) Inventors: Mark Johan Van Raaij, Pays-Bas (NL); Stephen Cusack, Seyssinet (FR); Valérie Legrand, Strasbourg (FR); Philippe Leissner, Strasbourg (FR); Majid Mehtali, Amsterdam (NL)

(73) Assignees: Transgene S.A., Strasbourg (FR); European Molecular Biology Laboratory (EMBL), Heidelberg (DE)

( * ) Notice: Subject to any disclaimer, the term of this patent is extended or adjusted under 35 U.S.C. 154(b) by 0 days.

(21) Appl. No.: 09/830,391

(22) PCT Filed: Aug. 25, 2000

(86) PCT No.: PCT/FR00/02377
§ 371 (c)(1),
(2), (4) Date: Jul. 30, 2001

(87) PCT Pub. No.: WO01/16344
PCT Pub. Date: Mar. 8, 2001

(30) Foreign Application Priority Data

Aug. 27, 1999 (FR) .............................. 99 10859

(51) Int. Cl.⁷ .......................... C12N 13/00; C12N 7/00; C12N 15/00; C07K 14/075
(52) U.S. Cl. ................. 435/173.3; 435/440; 435/235.1; 530/300; 530/350
(58) Field of Search .............................. 435/456, 235.1, 435/320.1, 325, 375, 69.7, 69.1, 440, 173.3; 530/350, 300, 402; 536/23.1, 23.4, 23.72, 24.1

(56) References Cited

U.S. PATENT DOCUMENTS

| | | | |
|---|---|---|---|
| 5,712,136 A | | 1/1998 | Wickham et al. |
| 5,846,782 A | * | 12/1998 | Wickham et al. .......... 435/69.7 |
| 6,057,155 A | * | 5/2000 | Wickham et al. .......... 435/325 |
| 6,455,314 B1 | * | 9/2002 | Wickham et al. .......... 435/456 |

FOREIGN PATENT DOCUMENTS

| | | |
|---|---|---|
| WO | 95 21259 | 8/1995 |
| WO | 96 26281 | 8/1996 |
| WO | 98 07865 | 2/1998 |
| WO | 98 13499 | 4/1998 |

OTHER PUBLICATIONS

Genseq database alignment of SEQ ID NO: 1 with Ad2 fiber protein, accession No: A93722 of Herisse et al. submitted Jul. 29, 1981.*

SPTREMBL database alignment of SEQ ID No.: 1 with Ad2 fiber protein, accession No.: Q96590 of Boudin et al. submitted Feb. 1, 1997.*

Fallaux F.J. et al., "New helper cells and matched early region 1–deleted adenovirus vectors prevent generation of replication–competent adenoviruses" Human Gene Therapy, vol. 9. No. 13, Sep. 1, 1998, pp. 1909–1917, XP002111678, ISSN: 1043–0342, the whole document.

Stevenson S.C. et al, "Selective Targeting of Human Cells by a Chimeric Adenovirus Vector Containing a Modified Fiber Protein", Journal of Virology, vol. 71, No. 6, Jun. 1997, pp. 4782–4790, XP002911345, ISSN: 0022–538X, the whole document.

* cited by examiner

*Primary Examiner*—James Housel
*Assistant Examiner*—Shanon Foley
(74) *Attorney, Agent, or Firm*—Burns, Doane, Swecker & Mathis, L.L.P.

(57) ABSTRACT

The present invention relates to a modified fiber of an adenovirus, comprising at least one mutation at one or more residues within the region of said fiber stretching from pleated sheet A to pleated sheet B, and including loop AB.

5 Claims, No Drawings

SEQUENCE LISTING

<160> NUMBER OF SEQ ID NOS: 28

<210> SEQ ID NO 1
<211> LENGTH: 581
<212> TYPE: PRT
<213> ORGANISM: Mastadenovirus 5 Ad5 fiber
<220> FEATURE:
<223> OTHER INFORMATION: Position on the map: 31063 to 33120 of the Ad5 genome.

<400> SEQUENCE: 1

```
Met Lys Arg Ala Arg Pro Ser Glu Asp Thr Phe Asn Pro Val Tyr Pro
1               5                   10                  15

Tyr Asp Thr Glu Thr Gly Pro Pro Thr Val Pro Phe Leu Thr Pro Pro
                20                  25                  30

Phe Val Ser Pro Asn Gly Phe Gln Glu Ser Pro Pro Gly Val Leu Ser
            35                  40                  45

Leu Arg Leu Ser Glu Pro Leu Val Thr Ser Asn Gly Met Leu Ala Leu
        50                  55                  60

Lys Met Gly Asn Gly Leu Ser Leu Asp Glu Ala Gly Asn Leu Thr Ser
65                  70                  75                  80

Gln Asn Val Thr Thr Val Ser Pro Pro Leu Lys Lys Thr Lys Ser Asn
                85                  90                  95

Ile Asn Leu Glu Ile Ser Ala Pro Leu Thr Val Thr Ser Glu Ala Leu
            100                 105                 110

Thr Val Ala Ala Ala Ala Pro Leu Met Val Ala Gly Asn Thr Leu Thr
        115                 120                 125

Met Gln Ser Gln Ala Pro Leu Thr Val His Asp Ser Lys Leu Ser Ile
    130                 135                 140

Ala Thr Gln Gly Pro Leu Thr Val Ser Glu Gly Lys Leu Ala Leu Gln
145                 150                 155                 160

Thr Ser Gly Pro Leu Thr Thr Thr Asp Ser Ser Thr Leu Thr Ile Thr
                165                 170                 175

Ala Ser Pro Pro Leu Thr Thr Ala Thr Gly Ser Leu Gly Ile Asp Leu
            180                 185                 190

Lys Glu Pro Ile Tyr Thr Gln Asn Gly Lys Leu Gly Leu Lys Tyr Gly
        195                 200                 205

Ala Pro Leu His Val Thr Asp Asp Leu Asn Thr Leu Thr Val Ala Thr
    210                 215                 220

Gly Pro Gly Val Thr Ile Asn Asn Thr Ser Leu Gln Thr Lys Val Thr
225                 230                 235                 240

Gly Ala Leu Gly Phe Asp Ser Gln Gly Asn Met Gln Leu Asn Val Ala
                245                 250                 255

Gly Gly Leu Arg Ile Asp Ser Gln Asn Arg Arg Leu Ile Leu Asp Val
            260                 265                 270

Ser Tyr Pro Phe Asn Ala Gln Asn Gln Leu Asn Leu Arg Leu Gly Gln
        275                 280                 285

Gly Pro Leu Phe Ile Asn Ser Ala His Asn Leu Asp Ile Asn Tyr Asn
    290                 295                 300

Lys Gly Leu Tyr Leu Phe Thr Ala Ser Asn Asn Ser Lys Lys Leu Glu
305                 310                 315                 320

Val Asn Leu Ser Thr Ala Lys Gly Leu Met Phe Asn Ala Thr Ala Ile
                325                 330                 335

Ala Ile Asn Ala Gly Asp Gly Leu Glu Phe Gly Ser Pro Asn Ala Pro
```

```
                      340               345               350
    Asn Thr Asn Pro Leu Lys Thr Lys Ile Gly His Gly Leu Glu Phe Asp
                355               360               365

Ser Asn Lys Ala Met Val Pro Lys Leu Gly Thr Gly Leu Ser Phe Asp
            370               375               380

Ser Thr Gly Ala Ile Thr Val Gly Asn Lys Asn Asp Lys Leu Thr
    385               390               395               400

Leu Trp Thr Thr Pro Ala Pro Ser Pro Asn Cys Arg Leu Asn Ala Glu
                    405               410               415

Lys Asp Ala Lys Leu Thr Leu Val Leu Thr Lys Cys Gly Ser Gln Ile
                420               425               430

Leu Ala Thr Val Ser Val Leu Ala Val Lys Gly Ser Leu Ala Pro Ile
                435               440               445

Ser Gly Thr Val Gln Ser Ala His Leu Ile Ile Arg Phe Asp Glu Asn
    450               455               460

Gly Val Leu Leu Asn Asn Ser Phe Leu Asp Pro Glu Tyr Trp Asn Phe
    465               470               475               480

Arg Asn Gly Asp Leu Thr Glu Gly Thr Ala Tyr Thr Asn Ala Val Gly
                    485               490               495

Phe Met Pro Asn Leu Ser Ala Tyr Pro Lys Ser His Gly Lys Thr Ala
                500               505               510

Lys Ser Asn Ile Val Ser Gln Val Tyr Leu Asn Gly Asp Lys Thr Lys
                515               520               525

Pro Val Thr Leu Thr Ile Thr Leu Asn Gly Thr Gln Glu Thr Gly Asp
            530               535               540

Thr Thr Pro Ser Ala Tyr Ser Met Ser Phe Ser Trp Asp Trp Ser Gly
    545               550               555               560

His Asn Tyr Ile Asn Glu Ile Phe Ala Thr Ser Ser Tyr Thr Phe Ser
                    565               570               575

Tyr Ile Ala Gln Glu
                580

<210> SEQ ID NO 2
<211> LENGTH: 60
<212> TYPE: DNA
<213> ORGANISM: Artificial Sequence
<220> FEATURE:
<223> OTHER INFORMATION: Primer.  Synthetic oligonucleotide oTG7000
      (codes for PSASASASAPGS)

<400> SEQUENCE: 2
aacgattctt tagctgccgg gagcagaggc ggaggcggag gcgctgggtt cttgggcaat      60

<210> SEQ ID NO 3
<211> LENGTH: 57
<212> TYPE: DNA
<213> ORGANISM: Artificial Sequence
<220> FEATURE:
<223> OTHER INFORMATION: Primer.  Synthetic oligonucleotide oTG7001
      (codes for GRP).

<400> SEQUENCE: 3
aacgattctt tacatcaggt ggcccacagc ccagtggttt ccgctgccgg gagcaga         57

<210> SEQ ID NO 4
<211> LENGTH: 20
<212> TYPE: DNA
<213> ORGANISM: Artificial Sequence
<220> FEATURE:
```

-continued

<223> OTHER INFORMATION: Primer. Synthetic oligonucleotide oTG10776.

<400> SEQUENCE: 4
ccttccacgg gaagattgta                                                      20

<210> SEQ ID NO 5
<211> LENGTH: 20
<212> TYPE: DNA
<213> ORGANISM: Artificial Sequence
<220> FEATURE:
<223> OTHER INFORMATION: Primer. Synthetic oligonucleotide oTG10781.

<400> SEQUENCE: 5
ggggtgtctg tcttcacact                                                      20

<210> SEQ ID NO 6
<211> LENGTH: 26
<212> TYPE: DNA
<213> ORGANISM: Artificial Sequence
<220> FEATURE:
<223> OTHER INFORMATION: Primer. Synthetic oligonucleotide oTG11065.

<400> SEQUENCE: 6
gggaagcttg aggttaacct aagcac                                               26

<210> SEQ ID NO 7
<211> LENGTH: 28
<212> TYPE: DNA
<213> ORGANISM: Artificial Sequence
<220> FEATURE:
<223> OTHER INFORMATION: Primer. Synthetic oligonculeotide oTG11066.

<400> SEQUENCE: 7
gggtctagag ctgccgggag cagaggcg                                             28

<210> SEQ ID NO 8
<211> LENGTH: 29
<212> TYPE: DNA
<213> ORGANISM: Artificial Sequence
<220> FEATURE:
<223> OTHER INFORMATION: Primer. Synthetic oligonucleotide oTG11067.

<400> SEQUENCE: 8
gggctcgagt tatgtttcaa cgtgtttat                                            29

<210> SEQ ID NO 9
<211> LENGTH: 24
<212> TYPE: DNA
<213> ORGANISM: Artificial Sequence
<220> FEATURE:
<223> OTHER INFORMATION: Primer. Synthetic oligonucleotide oTG11068.

<400> SEQUENCE: 9
gtgcccgggg agtttattaa tatc                                                 24

<210> SEQ ID NO 10
<211> LENGTH: 31
<212> TYPE: DNA
<213> ORGANISM: Artificial Sequence
<220> FEATURE:
<223> OTHER INFORMATION: Primer. Synthetic oligonucleotide oTG11069
      (EGF cloning) derived from Homo sapiens.

<400> SEQUENCE: 10
gcgtctagaa atagtgactc tgaatgtccc c                                         31

<210> SEQ ID NO 11
<211> LENGTH: 46
<212> TYPE: DNA
<213> ORGANISM: Artificial Sequence
<220> FEATURE:
<223> OTHER INFORMATION: Primer. Synthetic oligonucleotide oTG11070
(EGF cloning) derived from Homo sapiens.

<400> SEQUENCE: 11
gcgctcgagc acaaacgatt ctttagcgca gttcccacca cttcag     46

<210> SEQ ID NO 12
<211> LENGTH: 72
<212> TYPE: DNA
<213> ORGANISM: Artificial Sequence
<220> FEATURE:
<223> OTHER INFORMATION: Primer. Synthetic oligunucleotide oTG11992.

<400> SEQUENCE: 12
cataacacaa acgattcttt atgttcgtgt tggtggttct cgagcgcaat agctgccggg     60
agcagaggcg ga     72

<210> SEQ ID NO 13
<211> LENGTH: 57
<212> TYPE: DNA
<213> ORGANISM: Artificial Sequence
<220> FEATURE:
<223> OTHER INFORMATION: Primer. Synthetic oligonucleotide oTG11991.

<400> SEQUENCE: 13
cataacacaa acgattcttt aatatacgtc tagatagctg ccgggagcag aggcgga     57

<210> SEQ ID NO 14
<211> LENGTH: 42
<212> TYPE: DNA
<213> ORGANISM: Artificial Sequence
<220> FEATURE:
<223> OTHER INFORMATION: Primer. Synthetic oligonucleotide oTG12499
derived from Mastadenovirus.

<400> SEQUENCE: 14
gcatttagtc tacagttagg ctctggagct ggtgtggtcc ac     42

<210> SEQ ID NO 15
<211> LENGTH: 39
<212> TYPE: DNA
<213> ORGANISM: Artificial Sequence
<220> FEATURE:
<223> OTHER INFORMATION: Primer. Synthetic oligonucleotide oTG12498
derived from Mastadenovirus.

<400> SEQUENCE: 15
gtctacagtt aggagatggc tttggtgtgg tccacaaag     39

<210> SEQ ID NO 16
<211> LENGTH: 47
<212> TYPE: DNA
<213> ORGANISM: Artificial Sequence
<220> FEATURE:
<223> OTHER INFORMATION: Primer. Synthetic oligonucleotide oTG12740
derived from Mastadenovirus.

<400> SEQUENCE: 16
ctacagttag gagatggagc gggcccggtc cacaaagtta gcttatc     47

<210> SEQ ID NO 17
<211> LENGTH: 23
<212> TYPE: DNA
<213> ORGANISM: Artificial Sequence
<220> FEATURE:
<223> OTHER INFORMATION: Primer.  Synthetic oligonucleotide oTG 11102
      (hexon cloning) derived from Mastadenovirus.

<400> SEQUENCE: 17
cggttcatcc ctgtggaccg tga                                           23

<210> SEQ ID NO 18
<211> LENGTH: 38
<212> TYPE: DNA
<213> ORGANISM: Artificial Sequence
<220> FEATURE:
<223> OTHER INFORMATION: Primer.  Synthetic oligonucleotide oTG11103
      (hexon cloning) derived from Mastadenovirus.

<400> SEQUENCE: 18
ggcctctaga gttgagaaaa attgcatttc cacttgac                           38

<210> SEQ ID NO 19
<211> LENGTH: 23
<212> TYPE: DNA
<213> ORGANISM: Artificial Sequence
<220> FEATURE:
<223> OTHER INFORMATION: Primer. Synthetic oligonucleotide oTG11104
      (hexon cloning) derived from Mastadenovirus.

<400> SEQUENCE: 19
ggtattgtac agtgaagatg tag                                           23

<210> SEQ ID NO 20
<211> LENGTH: 23
<212> TYPE: DNA
<213> ORGANISM: Artificial Sequence
<220> FEATURE:
<223> OTHER INFORMATION: Primer.  Synthetic oligonucleotide oTG11105
      derived from Mastadenovirus.

<400> SEQUENCE: 20
cgttggaagg actgtacttt agc                                           23

<210> SEQ ID NO 21
<211> LENGTH: 38
<212> TYPE: DNA
<213> ORGANISM: Artificial Sequence
<220> FEATURE:
<223> OTHER INFORMATION: Primer.  Synthetic oligonucleotide oTG11106
      (cDNA EGF cloning) derived from Homo sapiens.

<400> SEQUENCE: 21
cgcgtctaga ggcgaatagt gactctgaat gtcccctg                           38

<210> SEQ ID NO 22
<211> LENGTH: 45
<212> TYPE: DNA
<213> ORGANISM: Artificial Sequence
<220> FEATURE:
<223> OTHER INFORMATION: Primer.  Synthetic oligonucleotide oTG11107
      (cDNA EGF cloning) derived from Homo sapiens.

<400> SEQUENCE: 22
ccactgtaca ataccacttt agggcgcagt tcccaccact tcagg                   45

<210> SEQ ID NO 23

```
<211> LENGTH: 21
<212> TYPE: DNA
<213> ORGANISM: Artificial Sequence
<220> FEATURE:
<223> OTHER INFORMATION: Primer.  Synthetic oligonucleotide oTG7171
      (deletion of the fiber) derived from Mastadenovirus.

<400> SEQUENCE: 23
atggttaact tgcaccagtg c                                            21

<210> SEQ ID NO 24
<211> LENGTH: 27
<212> TYPE: DNA
<213> ORGANISM: Artificial Sequence
<220> FEATURE:
<223> OTHER INFORMATION: Primer.  Synthetic oligonucleotide oTG7275
      (deletion of the fiber) derived from Mastadenovirus.

<400> SEQUENCE: 24
gggctcgagc tgcaacaaca tgaagat                                      27

<210> SEQ ID NO 25
<211> LENGTH: 27
<212> TYPE: DNA
<213> ORGANISM: Artificial Sequence
<220> FEATURE:
<223> OTHER INFORMATION: Primer.  Synthetic oligonucleotide oTG7276
      (deletion of the fiber) derived from Mastadenovirus.

<400> SEQUENCE: 25
ccgctcgaga ctcctccctt tgtatcc                                      27

<210> SEQ ID NO 26
<211> LENGTH: 20
<212> TYPE: DNA
<213> ORGANISM: Artificial Sequence
<220> FEATURE:
<223> OTHER INFORMATION: Primer.  Synthetic oligonucleotide oTG7049
      (deletion of the fiber) derived from Mastadenovirus.

<400> SEQUENCE: 26
ctgcccggga gtttattaat                                              20

<210> SEQ ID NO 27
<211> LENGTH: 42
<212> TYPE: DNA
<213> ORGANISM: Artificial Sequence
<220> FEATURE:
<223> OTHER INFORMATION: Primer.  Synthetic oligonucleotide oTG7416
      (deletion of pleated sheet H) derived from Mastadenovirus.

<400> SEQUENCE: 27
tgtttcctgt gtaccgttgg atcctttagt tttgtctccg tt                     42

<210> SEQ ID NO 28
<211> LENGTH: 64
<212> TYPE: DNA
<213> ORGANISM: Artificial Sequence
<220> FEATURE:
<223> OTHER INFORMATION: Primer.  Synthetic oligonucleotide oTG10352
      (pleated sheet H5 to H3) derived from Mastadenovirus.

<400> SEQUENCE: 28
tgtttcctgt gtaccgttta gcatcacggt cacctcgaga ggtttagttt tgtctccgtt  60
taag                                                               64
```

MODIFIED ADENOVIRAL FIBRE AND USES THEREOF

This application is a U.S. national stage application of PCT International Application No. PCT/FR00/03377 filed Aug. 25, 2000.

The present invention relates, in particular, to an adenoviral fiber mutated in the regions involved in recognizing and binding to the natural cellular receptor for adenoviruses. It also relates to the adenoviral particles bearing, at their surface, such a fiber, optionally combined with a ligand which confers modified, or even targeted, host specificity on said particles. The invention is of most particular value in the context of the development of vectors which can be used in the context of gene therapy.

Adenoviral vectors are widely used in many gene therapy applications. They have been demonstrated in many animal species and are relatively nonpathogenic, and nonintegrating, and replicate both in dividing and in quiescent cells. In addition, they have a broad host spectrum and are capable of infecting a very great number of cell types, such as for example epithelial cells, endothelial cells, myocytes, hepatocytes, nerve cells and synoviocytes (Bramson et al., 1995, Curr. Op. Biotech. 6, 590–595).

The adenoviral genome consists of a double stranded, linear DNA molecule of approximately 36 kb containing two inverted repeat regions (referred to as ITRs for Inverted Terminal Repeat) framing the genes encoding the viral proteins. The early genes are divided into four regions dispersed in the adenoviral genome (E1 to E4; E for early), including 6 transcriptional units provided with their own promoters. The late genes (L1 to L5; L for late) cover, in part, the early transcription units and are, mostly, transcribed from the major late promoter (MLP).

Adenoviruses have been the subject of many studies and many scientific teams have developed adenoviral vectors which are replication-defective, i.e. in which the genome has been manipulated such that these adenoviral vectors are incapable of dividing or of proliferating in the cells which they infect. Defective adenoviral vectors are in particular obtained by deleting at least the E1 region (for examples of defective adenoviral vectors, see, in particular, patent applications WO 94/28152 and WO 94/12649).

More recently, other uses of adenoviral particles have been described, in particular in the context of implementing gene therapy protocols.

Thus, patent application WO 95/21259 describes a method for introducing a nucleic acid into a cell, which is based on combining adenoviral particles and nucleic acid, more particularly naked nucleic acid. This method is based mainly on the capacity of the adenoviral particle to transport molecules to the cell nucleus after endocytosis. Curiel et al. (1992 Hum. Gene Ther., 3: 147–154) and Wagner et al. (1992, Proc.

Natl. Acad. Sci., 89; 6099–6103), have, themselves also, shown that combining plasmid with inactivated adenoviral particles allows the endosome to be lysed before fusion with the lysosomes and, therefore, allows the plasmid to escape degradation. This ingenious device makes it possible to increase the efficiency of transfection of the plasmid 100-to 1000-fold in vitro. Preferably, in order for the cellular transfection to be independent of the adenoviral process and to indeed involve the use of a ligand chosen so as to allow targeting of the transfection, an antibody which neutralizes the adenoviral infection can be added to the complex (Michael et al., 1993, J. Biol. Chem., 268: 6866–6869). The contents of these publications and patent applications are incorporated by reference in their entirety, into the present application.

The infectious cycle of adenoviruses is based on two essential steps. The early phase precedes replication initiation and allows the production of the early proteins which regulate replication and transcription of the viral DNA. Replication of the genome is followed by the late phase during which the structural proteins which constitute the basis of the viral particles are synthesized. Assembly of the new virions takes place in the nucleus. Initially, the viral proteins assemble so as to form empty capsids of icosahedral structure, in which the newly formed genome is encapsidated. The adenoviruses released are capable of infecting other permissive cells.

During infection, the fiber and the penton base of the adenoviral particle, present at the surface of the capsids, play a critical role in the cellular attachment of the virions and their internalization (Wickham et al., 1993, Cell, 73, 309–319). Firstly, the adenovirus binds to a cellular receptor (the CAR) present at the surface of the permissive cells, via the fiber in its trimeric form (Philipson et al., 1968, J. Virol. 2, 1064–1075; Defer et al., 1990, J. Virol, 64, 3661–3673). The viral particle is then internalized by endocytosis, due to binding of the penton base to the $\alpha_v\beta_3$ and $\alpha_v\beta_5$ cellular integrins (Mathias et al., 1994, J. Virol. 68, 6811–6814).

The adenoviral fiber is composed of three distinct domains (Chroboczek et al., 1995, Current Top. Microbiol. Immunol. 199, 165–200):

(a) at its N-terminal end, is the tail, the sequence of which is very conserved from one adenoviral serotype to the other. It interacts with the penton base and ensures the anchoring of the molecule in the capsid;

(b) in the center, is the shaft. It is a rod-like structure composed of a certain number of pleated-sheet repeats, the number of which varies according to the serotypes under consideration;

(c) at its C-terminal end is the Knob, which has a spherical globular structure containing the trimerization signals (Hong and Engler, 1996, J. Virol. 70, 7071–7078; Novelli and Boulanger, 1991, J. Biol. Chem. 266, 9299–9303; Novelli and Boulanger, 1991, Virology 185, 365–376), and is responsible for the binding to permissive cells (Henry et al., 1994, J. Virol 68, 5239–5246; Louis et al., 1994, J. Virol. 68, 4104–4106).

Several teams have already described adenoviral particles for which the native fiber has been modified so as to modify their natural tropism and change the binding specificity of this fiber such that it recognizes a different cellular receptor.

WO 94/10323 describes type 5 (Ad5) adenoviral particles in which the fiber has been mutated so as to comprise the sequence of a fragment of antibody specific for a given antigen (of scFv type), inserted at the end of one of the 22 repetitive units of the shaft. These mutants have a modified specificity of infection of the adenoviral particles and are capable of attaching to cells exhibiting the target antigen.

U.S. Pat. No. 5,543,328. describes a chimeric adenoviral fiber in which the Knob domain is replaced with the tumor necrosis factor (TNF) sequence, or that of the ApoE peptide, so as to redirect the attachment of the modified adenoviral particles toward cells expressing the cellular receptor for TNF or the LDL (low density lipoprotein) receptor, respectively, present at the surface of hepatic cells.

WO 95/26412 describes a fiber modified by incorporating a ligand at the C-terminal end.

WO 96/26281 describes a chimeric fiber obtained by replacing a portion of the native fiber, and in particular of the knob, with the equivalent portion of an adenoviral fiber of another serotype and, optionally, inserting a vitronectin-specific RGD peptide at the C-terminal end.

In addition, French patent application FR 2758821 (97 01005) has demonstrated the role of the class I major histocompatibility complex antigens and of the III modules of fibronectin as a primary receptor and a cofactor, respectively, for adenoviruses. In an identical way, Tomko et al. (1997, Proc. Natl. Acad. Sci 94, 3352–3356), Bergelson et al. (1997, Science 275, 1320–1323) and Roelvink et al. (1998, J. Virol. 72, 7909–7915) have described another receptor for the fiber of various adenoviral serotypes. It is a 46 kDa surface molecule, CAR (Coxsackie and Adenovirus Receptor).

Finally, Xia et al. (1994, Structure 2, 1259–1270) have determined the crystallographic three-dimensional structure of the adenoviral knob. Each monomer includes 8 antiparallel β-pleated sheets, referred to as A to D and G to J, and 6 major loops of 8 to 55 residues. For example, loop CD connects pleated sheet C to pleated sheet D. It is indicated that minor pleated sheets E and F are considered to form part of loop DG located between pleated sheets D and G. By way of indication, Table 1 gives the location of the structures in the amino acid sequence of the Ad5 fiber, as shown in sequence identifier No. 1 (SEQ ID NO: 1), the +1 representing the Met initiating residue. In general, the pleated sheets form an organized and compact structure, whereas the loops are more flexible. These terms are conventional in the field of protein biochemistry, and are defined in fundamental works (see, for example, Stryer, Biochemistry, 2nd Edition, Chap. 2, p. 11 to 39, Ed Freeman and Company, San Francisco).

TABLE 1

| β pleated sheet | | Loop | |
| --- | --- | --- | --- |
| nomenclature | Residues | nomenclature | Residues |
| A | 400 to 403 | AB | 404 to 418 |
| B | 419 to 428 | — | — |
| C | 431 to 440 | CD | 441 to 453 |
| D | 454 to 461 | DG | 462 to 514 |
| G | 515 to 521 | GH | 522 to 528 |
| H | 529 to 536 | HI | 537 to 549 |
| I | 550 to 557 | IJ | 558 to 572 |
| J | 573 to 578 | | |

The four β-pleated sheets A, B, C and J constitute the V pleated sheets directed toward the viral particle. The other four (D, G, H and I) form the R pleated sheets, which are presumed to face the cellular receptor. The V pleated sheets seem to play an important role in the trimerization of the structure, while the R pleated sheets are thought to be involved in the interaction with the receptor.

The present invention provides novel mutants of the adenoviral fiber which allow, in particular, the production of viral particles which have the following properties:
(i) the adenoviral particle comprising said mutated fiber does not substantially attach to the natural cellular receptors, i.e. the host specificity of these adenoviral particles bearing the mutated fiber is decreased, or even inhibited, in comparison to the host specificity of the adenoviral particles carrying the wild-type, i.e. nonmutated, fiber;
(ii) when the adenoviral particle comprising said mutated fiber also comprises a ligand specific for an antiligand, it is possible to confer on said modified particle a novel tropism for one or more specific cell types bearing, at its (their) surface, said antiligand, in comparison to the nonmutated adenoviral particle.

The expression "the mutated fiber does not substantially attach to the natural cellular receptors" is intended to indicate that the fiber is modified so as to decrease or abolish its ability to bind to the natural cellular receptor. Such a property can be verified by studying the infectivity or the cellular binding of the corresponding adenoviral particles, using the techniques of the art, and, in particular, with infection competition experiments for the virus bearing the modified fiber, carried out in the presence of a competitor consisting of all or part of the wild-type adenoviral fiber (for more detail relating to this measuring technique, see the Experimental Section of the present application). The loss of the natural specificity can also be evaluated with cell attachment studies carried out in the presence of labeled viruses (for example labeled with $^3$H thymidine, according to the technique of Roelvink et al., 1996, J. Virol. 70, 7614–7621) or with studies of infectivity of permissive cells or of cells expressing the surface molecule targeted by the ligand (see the examples which follow). Advantageously, "a mutated fiber does not substantially attach to the natural cellular receptors" when the percentage of residual infection, measured with a competition experiment as disclosed in the examples which follow, is between approximately 0 and 60%, preferably between 0 and 40%, and entirely preferably between 0 and 20%. In addition, according to an advantageous embodiment, the properties of trimerization and of binding to the penton-base of the mutated adenoviral fiber are not affected. These properties are easily verified according to the technique used in the examples which follow.

The present invention has, in particular, the advantage of providing novel products, the properties of which make it possible to decrease the therapeutic amounts of adenovirus to be administered and to target the infection of the vector to the cells to be treated. This specificity is particularly essential when an adenoviral vector is used which is capable of expressing a cytotoxic gene, in order to avoid the propagation of the cytotoxic effect to the healthy and nontargeted cells. In addition, the teachings of the present invention allow the development of other targeting systems intended for developing methods of treatment by administration of recombinant viral or nonviral vectors.

Firstly, the present invention relates to the modified fiber of an adenovirus, comprising at least one mutation at one or more residues within the region of said fiber stretching from pleated sheet A to pleated sheet B, and including loop AB. More particularly, the mutations are preferably produced at one or more residues within loop AB.

For the purposes of the invention, the terms "residues" and "amino acids" are synonyms. The terms "pleated sheets" and "loops" are defined according to Xia et al. 1994, Structure 2, 1259–1270.

The term "nucleic acid sequence" is intended to refer to a synthetic or isolated natural, linear or circular, double-stranded or single-stranded fragment of DNA and/or of RNA and/or PNA which refers to a specific series of nucleotides, which may or may not be modified, making it possible to define a fragment or a region of a nucleic acid without size limitation. According to a preferred embodiment, it is a nucleic acid chosen from the group consisting of a cDNA (complementary DNA); a genomic DNA; a plasmid DNA; an RNA and a viral genome.

The term "portion" of an amino acid sequence is intended to mean an amino acid sequence comprising a minimum of 6 consecutive amino acids, preferably 10, more preferably 15, even more preferably 20, and most preferably 30, and/or having the same biological activity as the sequence from which said portion is derived, in particular the ability to recognize and to bind to the target cells of the virus.

The term "portion" of a nucleic acid sequence is intended to mean a nucleic acid sequence comprising a minimum of 18 consecutive nucleotides, preferably 30, more preferably 45, even more preferably 60, and most preferably 90, and/or encoding an amino acid sequence having the same biological activity as the amino acid sequence encoded by the nucleic acid sequence from which said portion is derived.

The fiber according to the present invention can derive from an adenovirus of human, canine, avian, bovine, murine, ovine, porcine or simien origin, or be hybrid and comprise fragments of diverse origins, including fragments of heterologous origin, i.e. not derived from an adenoviral fiber, or derived from nonadenoviral fibers. With regard to human adenoviruses, those of serotype C and, in particular, type 2 or 5 adenoviruses (Ad2 or Ad5) are preferably used. The fiber of Ad2 includes 580 amino acids (aa), the sequence of which is disclosed in Herisse et al. (1981, Nucleic Acid Res. 9, 4023–4042, incorporated into the present application by reference). That of Ad5 has been determined by Chroboczek and Jacrot (1987, Virology, 161, 549–554, incorporated by reference) and has 582 amino acids (see sequence identifier 1; SEQ ID NO: 1). In order to simplify the presentation of the present application, only the positions relating to Ad5 are given. However, it is within the scope of those skilled in the art to identify the equivalent positions of the various pleated sheets and loops on the basis of the sequences of adenoviral fibers of other origins. When the fiber of the present invention is of animal origin, use is preferably made of bovine adenoviruses and, in particular, those of the BAV-3 strain. The latter have been the subject of many studies, and the sequence of the fiber is disclosed in international application WO 95/16048, the content of which is incorporated by reference. Of course, the fiber of the present invention can, besides the modifications described in the present invention, have other modifications with respect to the native sequence, as long as they do not affect the characteristics of the fiber proposed in the application. In addition, it is within the scope of those skilled in the art to identify the adenoviral fiber sequences available on databases such as, for example, GenBank, and to identify the equivalent positions of the various pleated sheets and loops as described later. By way of information, mention is made, for example, of the GenBank references for the adenoviral fiber sequences of human serotype 2 (# AAA92223), 3 (# CAA26029), 5 (#M18369), 31 (#CAA54050 or 41 (#X17016). The contents of the publications or of the GenBank references mentioned above are incorporated, in their entirety, into the present application by reference. The invention also relates to a modified fiber according to the present invention, which also contains other mutations, such as for example those described in patent application WO 98/44121. More particularly, such a fiber according to the invention is characterized in that it also comprises one or more mutations in:

a) loops CD, DG, GH, HI and/or IJ and/or b) pleated sheets C, D, G, H, I and/or J.

For the purpose of the present invention, the term "mutation" refers to a deletion, substitution or addition of one or more residues, or a combination of these possibilities.

According to a first embodiment of the invention, the adenoviral fiber according to the invention derives from a fiber of a type 5 adenovirus (Ad5) comprising all or part of the sequence as shown in sequence identifier No. 1 (SEQ ID NO: 1), and is characterized in that it is modified by mutation of one or more residues of the region between residues 400 and 428, more particularly between residues 404 and 418, and preferably between residues 404 and 408, of SEQ ID NO: 1. Entirely preferably, such an adenoviral fiber has the properties (i) and (ii) set out above.

Preferably, the invention relates to a fiber of a type 5 adenovirus, characterized in that the mutated residue is selected from the threonine residue at position 404, the alanine residue at position 406 and the serine residue at position 408.

Because of their spatial location in the native fiber, these residues are capable of recognizing and/or interacting directly or indirectly with the natural cellular receptor for the adenovirus in question.

According to a particular case of the invention, the mutation produced is a substitution of at least one amino acid. In this capacity, mention may be made of the following examples of a fiber of a type 5 adenovirus, for which:

the serine residue at position 408 is substituted with a residue having at least two carboxyl groups, and in particular with a residue selected from the group consisting of aspartic acid and glutamic acid, and/or the threonine residue at position 404 is substituted with a glycine residue and/or the alanine residue at position 406 is substituted with a lysine residue.

It is also possible to introduce several substitutions into the targeted region of the fiber, in particular at the amino acids forming a bend, preferable of $\alpha\alpha$ type.

In accordance with the invention, it is preferable not to drastically modify the three-dimensional—structure of the adenoviral fiber; thus, the amino acids forming a bend will be replaced with residues forming a similar structure, such as those mentioned in Xia et al. (1994).

The fiber of the present invention can also be modified by deletion. The region removed can concern all or part of the exposed domain and, in particular, of loop AB.

According to an advantageous embodiment, when one at least of the modifications is deletion of at least three consecutive residues of a loop and/or of a pleated sheet, the deleted residues can be replaced with residues of an equivalent loop and/or pleated sheet derived from a fiber of a second adenovirus capable of interacting with a cellular receptor other than that recognized by the first adenovirus. This makes it possible to maintain the structure of the fiber according to the invention, while at the same time confering upon it a host specificity corresponding to that of the second adenovirus. As indicated in Xia et al. (1994), the infection of type 2 and type 5 adenoviruses is different from that of type 3 and type 7 adenoviruses. Thus, the residues deleted from an Ad5 or Ad2 fiber deleted of at least three consecutive residues among those specified above can be substituted with the residues derived from an equivalent region of the Ad3 or Ad7 fiber, so as to decrease the ability of said fiber to bind the receptor for Ad5 and to confer upon it a novel specificity toward the cellular receptor for Ad3 or Ad7.

The present invention also relates to a fiber of an adenovirus having a substantially decreased ability to bind to the natural cellular receptor, as shown above, but nevertheless capable of trimerizing. Such a property is, in particular, determined using the technique described in the experimental section of the application.

According to an equally advantageous embodiment, the fiber according to the invention also comprises a ligand. For the purpose of the present invention, the term "ligand" defines any entity capable of recognizing and binding, preferably with high affinity, a cellular antiligand other than the natural cellular receptor for the nonmutated adenoviral fiber. This antiligand can be expressed or exposed at the surface of the cell the targeting of which is desired (cell surface marker, receptor, antigenic peptide presented by histocompatibility antigens, etc.), naturally or subsequent to a modification of said target aimed at making it express or expose such an antiligand at its surface. In accordance with the aims pursued by the present invention, a ligand can be an antibody or an antibody fragment, a lipid, a glycolipid, a hormone, a polypeptide, a polymer (PEG, polylysine, PEI, etc.) or a sugar. The term "antibody" refers, in particular, to monoclonal antibodies, antibody fragments (such as, for example, Fab fragments) and single chain antibodies (scFv). These names and abbreviations are conventional in the field of immunology.

In the context of the present invention, it may be advantageous to target more particularly a tumor cell, an infected cell, a specific cell type or a category of cells bearing a specific surface marker. For example, if the host cell to be targeted is a cell infected with the HIV virus (Human Immunodeficiency Virus), the ligand can be a fragment of antibody against fusin, the CD4 receptor or against an exposed viral protein (envelope glycoprotein), or the portion of the HIV virus TAT protein stretching from residues 37 to 72 (Fawell et al., 1994, Proc. Natl. Acad. Sci. USA 91, 664–668). If it is a tumor cell, the choice will relate to a ligand which recognizes a tumor-specific antigen (for example the MUC-1 protein in the case of breast cancer, or certain epitopes of the HPV papilloma virus E6 or E7 proteins) or which is overexpressed (IL-2 receptor overexpressed in certain lymphoid tumors). If the intention is to target T lymphocytes, a T-cell receptor ligand can be used. Moreover, transferrin is a good candidate for hepatic targeting. In general, the ligands which can be used in the context of the invention are widely described in the literature and can be cloned using standard techniques. It is also possible to synthesize them chemically, and to couple them to the fiber according to the invention. In this respect, the coupling of galactosyl residues should confer hepatic specificity due to the interaction with asialoglycoprotein receptors. However, the preferred embodiment consists in inserting the ligand at the C-terminal end of the fiber according to the invention or as a replacement for the residues deleted when one at least of the modifications is a deletion of at least 3 consecutive residues.

Another subject of the invention relates to a peptide fragment characterized in that it comprises the region stretching from pleated sheet A to pleated sheet B, and including loop AB, of a modified fiber as described above. Such a peptide fragment has, in particular, the following properties:

(i) when this peptide fragment is incorporated in place of a region stretching from pleated sheet A to pleated sheet B, and including loop AB, of a given heterologous adenoviral fiber, the adenoviral particle comprising said mutated fiber does not substantially attach to the natural cellular receptors (ii) when the adenoviral particle comprising said mutated fiber according to (i) also comprises a ligand specific for an antiligand, it is possible to confer upon said modified particle a novel tropism for one or more specific cell types bearing, at their surface, said antiligand, in comparison with the adenoviral particle which does not comprise such a mutated fiber.

The invention relates more specifically to such a peptide fragment characterized in that it is the sequence stretching from residue 388 to residue 592 of a fiber of a type 5 adenovirus (Ad5) comprising all or part of the sequence as shown in sequence identifier No. 1 (SEQ ID NO: 1) and comprising at least one mutation at one or more residues of the region between residues 400 and 428.

The present invention also relates to an adenoviral particle which comprises, at its surface, a mutated fiber according to the invention and, optionally, a ligand as defined above. According to a preferred case, this adenoviral particle lacks a functional native fiber. The mutated fiber of the invention can be expressed by the adenoviral genome itself, in particular when said adenoviral particle contains such a genome, or provided in trans by a complementation cell line, such as those defined hereinafter. According to a particular embodiment, the adenoviral particle of the invention is as shown above and is characterized in that said ligand is inserted into an adenoviral capsid protein other than the fiber, in particular the hexon or the penton.

According to a particular case of the invention, said adenoviral particle of the invention is "empty", i.e. it contains no nucleic acid. The use of such viral particles is in particular illustrated in document WO 95/21259, mentioned later. When, on the contrary, this adenoviral particle contains an adenoviral genome, reference will preferably be made to an adenoviral virus (or adenovirus) and, in the specific case in which said genome is also modified, reference will more especially be made to a recombinant adenoviral virus (or recombinant adenovirus).

Such cases are described in greater detail hereinafter. The invention therefore also relates to such adenoviruses and recombinant adenoviruses.

According to the invention, said ligand can be chemically coupled to said adenoviral particle. However, preference is given to the variant according to which the sequences encoding the ligand are inserted into the adenoviral genome, and preferably into the sequences encoding the modified fiber according to the invention, and more specifically in frame in order to preserve the reading frame. The insertion can take place at any site. However, the preferred insertion site is upstream of the stop codon at the C-terminal end, or in place of the deleted residues. It is also possible to envisage introducing the sequences of the ligand into other adenoviral sequences, in particular those encoding another capsid protein, such as the hexon or the penton.

Advantageously, the invention relates to a recombinant adenovirus which is replication-defective, i.e. incapable of autonomous replication in a host cell. The deficiency is obtained by a mutation or deletion of one or more essential viral genes and, in particular, of all or part of the E1 region in the adenoviral genome. Deletions in the E3 region can be envisaged in order to increase cloning capacities. However, it may be advantageous to conserve the sequences encoding the gp19k protein (Gooding and Wood, 1990, Critical Reviews of Immunology 10, 53–71) in order to modulate the immune responses of the host. Of course, the genome of an adenovirus according to the invention can also comprise further deletions or mutations affecting other regions, in particular the E2, E4 and/or L1–L5 regions (see, for example, WO 94/28152 or WO 94/12649, or Ensinger et al., 1972, J. Virol. 10, 328–339, describing the heat-sensitive mutation of the DBP gene of E2).

According to a preferred embodiment, a recombinant adenovirus of the invention comprises one or more gene(s) of interest placed under the control of the elements required for its (their) expression in a host cell. The gene in question can be of any origin, genomic, cDNA (complementary DNA) or hybrid (minigene lacking one or more introns). It can be attained using conventional techniques of molecular biology, or by chemical synthesis. It can encode an antisense RNA, a ribozyme or an MRNA which will then be translated into a polypeptide of interest. This polypeptide can be cytoplasmic or membrane-bound, or can be secreted by the host cell. Moreover, it can be all or part of a polypeptide as found naturally, of a chimeric polypeptide originating from the fusion of sequences of diverse origins, or of a polypeptide which is mutated with respect to the native sequence and which has improved and/or modified biological properties.

In the context of the present invention, it may be advantageous to use the genes encoding the following polypeptides:

- cytokines or lymphokines (α-, β- and γ-interferons, interleukins, and in particular IL-2, IL-6, IL-10 or IL-12, tumor necrosis factors (TNFs), colony stimulating factors (GM-CSF, C-CSF, M-CSF, etc.);
- cellular or nuclear receptors, in particular those recognized by pathogenic organisms (viruses, bacteria or parasites), and preferably by the HIV virus, or their ligands;
- proteins involved in a genetic disease (factor VII, factor VIII, factor IX, dystrophin or minidystrophin, insulin, CFTR (Cystic Fibrosis Transmembrane Conductance Regulator) protein, growth hormones (hGH));
- enzymes (urease, renin, thrombin, etc.);
- enzyme inhibitors (α1-antitrypsin, antithrombin III, viral protease inhibitors, etc.);
- polypeptides with an antitumor effect, capable of inhibiting, at least partially, the initiation or progression of tumors or cancers (antibodies, inhibitors acting on cell division or on transduction signals, tumor suppressor gene expression products, for example p53 or Rb, proteins which stimulate the immune system, etc.);
- class I or II major histocompatibility complex proteins or regulatory proteins acting on the expression of the corresponding genes;
- polypeptides capable of inhibiting a viral, bacterial or parasitic infection or its development (antigenic polypeptides having immunogenic properties, antigenic epitopes, antibodies, transdominant variants capable of inhibiting the action of a native protein by competition, etc.);
- toxins (herpes simplex virus 1 thymidine kinase (TK-HSV-1), ricin, cholera toxin, diptheria toxin, etc.) or immunotoxins; and
- markers (β-galactosidase, luciferase, etc.).

It should be pointed out that this list is not limiting and that other genes can also be used.

Moreover, a recombinant adenovirus according to the invention can also comprise a selection gene allowing the selection or identification of the infected cells. Mention may be made of the neo gene (encoding neomycin phosphotransferase) which confers resistance to the G418 antibiotic, the dhfr (dihydrofolate reductase) gene, the CAT (chloramphenicol acetyltransferase) gene, the pac (puromycinacetyltransferase) gene or the gpt (xanthine guanine phosphoribosyl transferase) gene. In general, the selection genes are known to those skilled in the art.

The expression "elements required for the expression of a gene of interest in a host cell" is intended to mean the set of elements allowing its transcription into RNA and the translation of an mRNA into protein. Among these, the promoter is of particular importance. In the context of the present invention, it can derive from any gene of eukaryotic, or even viral, origin and can be constitutive or regulatable. Moreover, it can be modified so as to improve the promoter activity, suppress a transcription-inhibiting region, make a constitutive promoter regulatable or vice versa, introduce a restriction site, etc. Alternatively, it can be the natural promoter of the gene to be expressed. Mention may be made, by way of examples, of the CMV (cytomegalovirus), RSV (Rous Sarcoma Virus), HSV-1 virus TK gene, SV40 virus (Simian Virus 40) early, and MLP adenoviral viral promoters, or the eukaryotic promoters of the murine or human PGK (phospho glycerate kinase), α1-antitrypsin (liver-specific) and immunoglobulin (lymphocyte-specific) genes.

Of course, a gene of interest used in the present invention can also comprise additional elements required for expression (intronic sequence, signal sequence, nuclear localization sequence, transcription termination sequence, translation initiation site of IRES or other type, etc.) or for its persistence in the host cell. Such elements are known to those skilled in the art.

The present invention also relates to a DNA fragment encoding a fiber or a peptide fragment according to the invention, and also to a vector for expressing such a fiber or such a fragment. Any type of vector can be used for this purpose, whether of plasmid or viral, integrating or nonintegrating, origin. Such vectors are commercially available or described in the literature. Similarly, those skilled in the art are capable of adjusting the regulatory elements required for the expression of the DNA fragment according to the invention. According to one particular case of the invention, a said vector will be an adenoviral vector capable of producing, under suitable culturing conditions, adenoviral particles according to the invention, namely adenoviruses or recombinant adenoviruses as described above.

The invention also relates to a process for preparing adenoviral particles according to the invention, in which:

- the adenoviral genome encoding a modified fiber according to the invention is transfected into a suitable cell line, for example the 293 line;
- said transfected cell line is cultured cultured under suitable conditions so as to allow the production of said adenovirus or of said recombinant adenovirus, and
- the empty particles are recovered by purifying the cell lysate on a density gradient, in particular a cesium chloride gradient for example.

The empty particles sediment, for example, at 1.3 g/ml of cesium chloride, while the recombinant adenoviruses (particles containing the Ad genome), themselves, sediment at 1.34 g/ml (D'Hallivin, 1995, Cur. Top. Microbiol. Immunol, 199, 47–66).

According to another process, it is possible to obtain empty particles after transfecting an adenoviral genome carrying a modified encapsidation sequence, and also containing a DNA fragment encoding a modified fiber according to the invention, into suitable cells. The modification of the encapsidation region makes it possible to decrease, or even eliminate, the phenomenon of encapsidation of the adenoviral genome in the particles (Gräble and Hearing, 1992, J. Virol. 66, 723–731). The production steps which follow the culturing are identical to those described above.

The invention also relates to a process for preparing an adenovirus or a recombinant adenovirus according to the invention, according to which:

- the genome of said adenovirus, which may or may not be recombinant and which may or may not be replication-defective, is transfected into a suitable cell line,
- said transfected cell line is cultured under suitable conditions so as to allow the production of said adenovirus or of said recombinant adenovirus (it is also possible to refer to adenoviral particles), and
- said adenovirus or said recombinant adenovirus is recovered from the culture of said transfected cell line and, optionally, said adenovirus is purified.

The choice of cell line depends, where appropriate, on the deficient functions of the adenovirus according to the invention. A complementation line capable of providing the defective function(s), in trans, will in particular be used. The 293 (ATCC CRL 1573) or PERC6 (ECACC 96022940) lines are most particularly suitable for complementing the E1 function (Graham et al., 1977, J. Gen. Virol. 36, 59–72 or WO 97/00326, respectively). For an E1, and E2 or E4 double deficiency, a cell line among those described in French Patent Application FR 2737222 (96 04413) can be used. It is also possible to use an auxiliary virus in order to complement the defective adenovirus according to the invention in any host cell, or a mixed system using a complementation cell and an auxiliary virus, in which the elements are dependent upon each other. The means for propagating a defective adenovirus are known to those skilled in the art, who can refer, for example, to Graham and Prevec, 1991 (Methods in Molecular Biology, vol. 7, p. 190–128; Ed. E. J. Murey, The Human Press Inc.). The adenoviral genome is preferably reconstituted in vitro in *Escherichia coli* (*E. coli*), by ligation or homologous recombination (see, for example, French Application FR 2727689 (94 14470)). The purification processes are described in the state of the art. Mention may be made of the density gradient centrifugation technique.

According to an alternative process, it is also possible to construct "empty" adenoviral particles artificially by associating carboxy- or amino-terminal ends of adenoviral capsid proteins, peptides or glycoproteins, with lipids. Such modified lipids, incorporating in particular the peptide fragments of the invention, can then be incorporated into a liposome. Such a technique has been described by Tikchonenko et al., 1988, Gene 63, 321–330 in the case of liposomes bearing, at their surface, influenza virus glycoproteins.

The present invention also relates to a cell line comprising, either in a form integrated into the genome or in the form of an episome, a DNA fragment encoding a fiber according to the invention, placed under the control of the elements allowing its expression. The said line can derive from a cell complementing one or more adenoviral functions selected from those encoded by the E1, E2, E4 and L1–L5 regions. It preferably derives from the 293 line or from the PERC6 line. Such a line can be used for preparing an adenovirus, in particular a recombinant adenovirus, the genome of which lacks all or part of the sequences encoding the fiber (so as to produce a nonfunctional fiber or not to produce a fiber).

For this reason, the invention also relates to a process for producing adenoviral particles containing an adenoviral genome lacking all or part of the sequences encoding a fiber, characterized in that:
said genome is transfected into a cell line given above,
said transfected cell line is cultured under suitable conditions so as to allow the production of said adenoviral particle, and
said adenoviral particle is recovered from the culture of said transfected cell line and, optionally, said adenoviral particle is purified.

The present invention also covers a host cell which can be infected with an adenovirus according to the invention or which can be obtained using a process according to the invention. It is advantageously a mammalian cell and, in particular, a human cell. It can be a primary or tumor cell and of any origin, for example hematopoietic (totipotent stem cell, leukocyte, lymphocyte, monocyte or macrophage, etc.), muscle, nasal, pulmonary, tracheal, hepatic, epithelial or fibroblast origin.

A subject of the invention is also a composition which comprises, as a therapeutic or prophylactic agent, a host cell, an adenoviral particle or an adenovirus, in particular a recombinant adenovirus, according to the invention, which can be obtained using a process according to the invention, in combination with a support which is acceptable from a pharmaceutical point of view. The composition according to the invention is, in particular, intended for the preventive or curative treatment of diseases such as genetic diseases (hemophilia, cystic fibrosis, diabetes or Duchenne, Becker, etc. myopathy), cancers, such as those induced by oncogenes or viruses, viral diseases, such as hepatitis B or C and AIDS (acquired immunodeficiency syndrome resulting from HIV infection), and recurrent viral diseases, such as viral infections caused by the herpesvirus.

A composition according to the invention can be manufactured conventionally. In particular, a therapeutically effective amount of the therapeutic or prophylactic agent is combined with a support which is acceptable from a pharmaceutical point of view. Such a support is nontoxic for the patient. It can be an injectable solution, an isotonic solution, the pH of which is compatible with use in vivo, a solution of dextrose, of glycerol, of mannitol, etc. A composition according to the invention can be administered locally, systemically or by aerosol, in particular via the intragastric, subcutaneous, intracardiac, intra-muscular, intravenous, intraperitoneal, intratumoral, intrapulmonary, intranasal or intratracheal route. The administration can take place in a single dose or in a dose repeated one or more times after a certain period of delay. The suitable route of administration and dose vary depending on various parameters, for example on the individual or on the disease to be treated, or on the gene(s) of interest to be transferred. In particular, the viral particles according to the invention can be formulated in the form of doses of between $10^4$ and $10^{14}$ pfu (plaque forming units), advantageously $10^5$ and $10^{13}$ pfu, and preferably $10^6$ and $10^{12}$ pfu. The formulation can also include an adjuvant or an excipient which is acceptable from a pharmaceutical point of view.

The composition according to the invention can also be formulated in the form of a solid or semi-solid preparation, in particular in the form of a gas, tablet, capsule, powder, gelatin capsule, granule, cream, solution, suppository or aerosol, depending on the route of administration selected.

In the pharmaceutical compositions of the present invention, the composition can be formulated with conventional pharmaceutical supports, known to those skilled in the art.

These supports comprise, in particular, a phrmaceutical vehicle such as gelatin, starch, lactose, magnesium stearate, talc, sucrose or gum arabic, or analogues.

It is also possible to obtain a preparation of gelatin capsules by mixing the composition with a diluent and pouring the mixture obtained into soft or hard gelatin capsules.

A preparation in the form of syrup or of elixir can contain the composition together with a sweetener, an antiseptic, and also a flavoring and a suitable colorant.

The water-dispersible powders or granules can contain the composition as a mixture with dispersants or wetting agents, or suspending agents, as well as with flavor enhancers or sweeteners.

For rectal administration, use is made of suppositories which are prepared with binders which melt at the rectal temperature, for example cacao butter or polyethylene glycols.

The composition can also be formulated in the form of microcapsules, optionally with one or more additive supports.

A subject of the present invention is also a composition characterized in that it also comprises at least one compound selected from a naked nucleic acid or a nucleic acid combined with at least one cationic compound.

With a view to their use in vivo, the adenoviral particles according to the invention can also be complexed with synthetic or natural compounds. Such adenoviral particles, and also their use, are, for example, described in O'Riordan et al., 1999, Human Gene Therapy, 10, 1349–1358 or in patent application WO 98/44143. The content of these documents is incorporated into the present application by reference.

Finally, the present invention relates to the use of a peptide fragment, of an adenoviral particle, of an adenovirus or of a host cell according to the invention, or of an adenovirus which can be obtained using a process according to the invention, for preparing a medicinal product intended for the treatment of the human or animal body. According to a first possibility, the medicinal product can be administered directly in vivo (for example by intravenous injection, into an accessible tumor, into the lungs by aerosol, etc.). The ex vivo approach can also be adopted, which consists in removing cells from the patient (bone marrow stem cells, peripheral blood lymphocytes, muscle cells, etc.), transfecting or infecting them in vitro according to the techniques of the art, and readministering them to the patient.

The invention also extends to a treatment method according to which a therapeutically effective amount of an adenovirus or of a host cell according to the invention is administered to a patient who needs such a treatment.

EXAMPLES

The aim of the examples which follow is to illustrate the various subjects of the present invention and, consequently, they are in no way limiting in nature.

The constructs described below are prepared according to the general techniques of genetic engineering and of molecular cloning, detailed in Maniatis et al., (1989, Laboratory Manual, Cold Spring Harbor, Laboratory Press, Cold Spring Harbor, N.Y.) or according to the manufacturer's recommendations when a commercial kit is used. The cloning steps using bacterial plasmids are preferably carried out in the *E. coli* strain 5 K (Hubacek and Glover, 1970, J. Mol. Biol, 50, 111–127) or BJ 5183 (Hanahan, 1983, J. Mol. Biol. 166, 557–580). The latter strain is preferably used for the homologous recombination steps. The NM522 strain (Strategene) is suitable for propagating the M13 phage vectors. The PCR amplification techniques are known to those skilled in the art (see, for example, PCR Protocols—A guide to methods and applications, 1990, edited by Innis, Gelfand, Sninsky and White, Academic Press Inc.). As regards the repair of restriction sites, the technique used consists in filling the overhanging 5' ends using the large fragment of *E. coli* DNA polymerase I (Klenow). The Ad5 nucleotide sequences are those used in the Genebank databank, under the reference M73260.

With regard to the cell biology, the cells are transfected according to standard techniques known to those skilled in the art. Mention may be made of the calcium phosphate technique (Maniatis et al., above), but any other protocol can also be used, such as the DEAE dextran technique, electroporation, methods based on osmotic shocks, microinjection or methods based on the use of cationic lipids. With regard to the culturing conditions, they are conventional. In the examples which follow, use is made of the 293 human line (ATCC CRL 1573) and of the Swiss 3T3 (ATCC CCL92), NR6 (Wells et al., 1990, Science 247, 962–964) and NR6-hEGFR (Schneider et al., 1986, Proc. Natl. Acad. Sci. USA 83, 333–336) murine lines. It is understood that other cell lines can also be used.

EXAMPLE 1

Construction of an Adenovirus Having a Host Tropism for Cells Expressing the Receptor for GRP (Gastrin Releasing Peptide)

A. Insertion of the Sequences encoding the GRP ligand (fiber-GRP)

The plasmid pTG6593 derives from p poly II (Lathe et al., 1987, Gene 57, 193–201) by the introduction of the complete gene encoding the Ad5 fiber, in the form of an EcoRI-SmaI fragment (nucleotides (nt) 30049 to 33093). The HindIII-SmaI fragment (nt 31994–33093) is isolated and cloned into M13TG130 (Kiney et al., 1983, Gene 26, 91–99), digested with these same enzymes, to give M13TG6526. The latter is subjected to site-directed mutagenesis using the oligonucleotide oTG7000 (SEQ ID NO: 2) (Sculptor in vitro mutagenesis kit, Amersham) in order to introduce a linker encoding a spacer arm of 12 amino acids. The mutated vector thus obtained, M13TG6527, is subjected to a second mutagenesis allowing the introduction of the sequence encoding the 10 residues of the GRP peptide (GNHWAVGHLM; Michael et al., 1995, Gene Ther. 2, 660–668). The oligonucleotide oTG001 (SEQ ID NO: 3) is used for this purpose. The HindIII-SmaI fragment is isolated from the mutated phage M13TG6528 and introduced, using the homologous recombination technique (Chartier et al., 1996, J. Virol. 70, 48054810), into the plasmid pTG6590 carrying the Ad5 adenoviral gene fragment stretching from nt 27081to 35935 and linearized with MunI (nt 32825). The SpeI-ScaI fragment (carrying nt 27082 to 35935 of the Ad5 genome, modified by introducing the spacer arm and the GRP peptide) is isolated from the vector above, referred to as pTG8599, and is then exchanged against the equivalent fragment of pTG6591, digested beforehand with these same enzymes. By way of indication, pTG6591 comprises the wild-type adenoviral sequences from positions 21562 to 35935. pTG4600 is obtained, from which the BstEII fragment is isolated (nt 24843to 35233). After homologous recombination with the plasmid pTG3602 which comprises the Ad5 genome (described in greater detail in International Application WO 96/17070), the vector pTG4601 is generated.

A cassette allowing the expression of the LacZ gene is introduced in place of the E1 adenoviral region by homologous recombination between the plasmid pTG4061 linearized with ClaI and a BsrGI-PstI fragment comprising the LacZ gene encoding β-galactosidase under the control of the Ad2 MLP promoter and the SV40 virus polyadenylation signal. This fragment is isolated from the vector pTG8526 containing the 5' end of the viral genomic DNA (nt 1 to 6241) in which the E1 region (nt 459 to 3328) is replaced with the LacZ expression cassette. Its construction is within the scope of those skilled in the art. The final vector is referred to as pTG4628.

The corresponding viruses AdTG4601 and AdTG4628 are obtained by transfecting the adenoviral fragments released from the plasmid sequences by PacI digestion, into the 293 line. By way of indication, AdTG4601 carries the complete Ad5 genome in which the fiber gene comprises, in its 3' end, a spacer arm followed by the GRP peptide. The recombinant virus AdTG4628 also carries the cassette for expressing the LacZ reporter gene under the control of the MLP adenoviral promoter.

B. Study of the tropism of the virus carrying the fiber-GRP

The presence of the GRP peptide in the adenoviral fiber makes it possible to target cells expressing, at their surface, the receptor for GRP. The expression of the messages encoding the latter is studied in 293 cells and in Swiss 3T3 murine cells (Zachary et al., 1985, Proc. Natl. Acad. Sci. USA 82, 7616–7620) by Northern blot. A mixture of 2 DNA fragments complementary to the sequence encoding the receptor for GRP, labeled with the $^{32}$p isotope using conventional techniques, is used as a probe. By way of indication, the fragments are produced by reverse PCR on total cellular RNAs using the oligonucleotides oTG10776 (SEQ ID NO: 4) and oTG10781 (SEQ ID NO: 5) (Battey et al., 1991, Proc. Natl. Acad. Sci. USA 88, 395–399; Corjay et al., 1991, J. Biol. Chem. 266, 18771–18779). The intensity of the mRNAs detected is much greater in the case of the Swiss-3T3 cells than in the case of the 293 cells, indicating the overexpression of the GRP receptor by the murine line.

Competition experiments are carried out on the 2 cell types. The competitor consists of the Ad5 fiber knob produced in *E. coli*, the adenoviral cellular receptor-binding properties of which have been shown (Henry et al., 1994, J. Virol 68, 5239–5246). The cells in monolayer are pre-incubated for 30 min in the presence of PBS or of increasing concentrations of recombinant Ad5 knob (0.1 to 100 μg/ml), in DMEM medium (Gibco BRL) supplemented with 2% fetal calf serum (FCS). Then, the virus AdTG4.628, the fiber of which contains the GRP peptide, is added at a multiplicity of infection of 0.001 infectious units/cell, for 24 h at 37° C. By way of control, and according to the same experimental conditions, the recombinant virus AdLacZ (Stratford-Perricaudet et al., 1992, J. Clin. Invest. 90, 626–630), which carries a native fiber gene, is used. The cells are then fixed and the expression of the LacZ gene is evaluated (Sanes et al., 1986, EMBO J. 5, 3133–3142). The number of blue cells is representative of the efficiency of the viral infection. Competition inhibition causes a decrease in the number of colored cells with respect to a noninfected control (PBS).

The addition of recombinant Ad5 knob at a concentration of 100 μg/ml strongly inhibits the infection of the 293 cells with the viruses AdLacZ and AdTG4628 (degree of inhibition of 95 and 98%). This suggests that the presence of the competitor prevents the interaction of the adenoviral fiber with its natural cellular receptor. On the other hand, the two viruses behave differently on the Swiss-3T3 cells. The infection of the virus AdTG4628 in the presence of 100 μg/ml of competitor is only partially inhibited, whereas, under the same experimental conditions, that of the virus AdLacZ having the native fiber is totally inhibited. These results suggest that the infection of the Swiss-3T3 cells with AdTG4628 is, in part, mediated by an independent receptor, probably the GRP receptor which these cells overexpress. In conclusion, the addition of the GRP ligand to the C-terminal end of the fiber promotes the infection of the cells expressing the GRP receptor, independently of the fiber-natural cellular receptor interaction.

EXAMPLE 2

Construction of an Adenovirus Having a Tropism for Tumor Cells Expressing Mucins Construction: insertion of the EPPT peptide, as described in U.S. Pat. No. 5,591,593, into the C-term of the fiber. This modification confers binding to mucins overexpressed on tumor cells.

OTG11992: SEQ ID NO 12
mutagenesis with m13TG6527 to give m13TG6572. Homologous recombination with pTG4213 to give pTG4278.

EXAMPLE 3

Construction of an Adenovirus Having a Tropism for Tumor Cells Expressing $\alpha_4\beta_1$ Integrins Construction: insertion of the LDV peptide, as described in U.S. Pat. No. 5,628,979, in the C-term of the fiber. This modification confers binding to $\alpha_4\beta_1$ integrins overexpressed on tumor cells.

OTG 1191: SEQ ID NO 13
mutagenesis with m3TG6527 to give M13TG13265.

EXAMPLE 4

Construction of an Adenovirus Having a host Tropism for Cells Expressing the EGF (Epidermal Growth Factor) Receptor.

This example describes a fiber carrying the EFG sequences at its C-terminal end. For this, the oligonucleotides oTG11065 (SEQ ID NO: 6) and oTG11066 (SEQ ID NO: 7) are used to amplify a HindIII-XbaI fragment from the plasmid M13TG6527. The oligonucleotides oTG11067 (SEQ ID NO: 8) and oTG11068 (SEQ ID NO: 9) make it possible to generate an XhoI-SmaI fragment (ranging from the stop codon up to nt 33093) from M13TG6527. The complementary DNA of EGF, obtained from the ATCC (#59957), is amplified in the form of an XhoI-XbaI fragment using the oligonucleotides oTG11069 (SEQ ID NO: 10) and oTG11070 (SEQ ID NO: 11). The 3 fragments digested with the appropriate enzymes are then religated to give a HindIII-SmaI fragment containing EGF fused to the C-terminal end of the fiber. The same procedure of homologous recombination as that described in example 1 is used to reposition this fragment in its genomic context.

However, the cloning steps can be simplified by introducing a unique BstBI site into the targeted region using conventional mutagenesis techniques. pTG4609 is obtained. The homologous recombination between pTG4609 linearized with BstBI and the HindIII-SmaI fragment above generates the plasmid pTG4225 carrying the wild-type E1 region. Its equivalent carrying the LacZ expression cassette, pTG4226 is obtained by homologous recombination with the pTG4213 digested with BstBI. The viruses AdTG4225 and AdTG4226 can be produced conventionally by transfecting a suitable cell line, for example, overexpressing the receptor for EGF.

In order to test the specificity of infection of these viruses, NR6 murine fibroblastic cells and Nr6-hEGFR cells expressing the receptor for human EGF can be used. Competition with the recombinant Ad5 knob or with EGF makes it possible to evaluate the involvement of the EGE or natural cellular receptors in mediating the infection of the viruses.

EXAMPLE 5

Modifications of the Fiber Knob so as to Eliminate the Binding to the Natural Cellular Receptor A. Modifications of the Fiber Sequences The mutation of region AB (amino acid 404–418) of the adenoviral fiber was undertaken in order to eliminate the ability of the fiber to bind its natural receptor, and the addition of a ligand will make it possible to modify the tropism of the corresponding adenoviruses.

replacement, in loop AB, of the serine at position 408 with the glutamic acid residue of serotype 3 using the oligo oTG12499 (SEQ ID NO: 14);

replacement, in loop AB, of the alanine at position 406 with the lysine residue of serotype 3 using the oligo oTG12498 (SEQ ID NO: 15);

replacement, in loop AB, of the threonine at position 404 with the glycine residue of serotype 3 using the oligo oTG12740 (SEQ ID NO: 16).

The mutageneses can be carried out on the vector M13TG6526 or M13TG6528. The first carries the wild-type HindIII-SmaI fragment and the second carries the same fragment modified by inserting the GRP sequences. The plasmids carrying the adenoviral genome can be reconstituted as described previously for the plasmids pTG4225 (wild-type E1) and pTG4226 (LacZ in place of the E1 region) (by homologous recombination with the plasmid pTG4609 or pTG4213). The viruses are generated by transfecting 293 cells, 293 cells expressing the wild-type fiber (Legrand et al., 1999; J. Virol., 73, 907–919) or cells overexpressing the receptor which binds the ligand in question. Such cells can be generated by transfection of the corresponding complementary DNA. Cells which do not naturally express the natural cellular receptor for adenoviruses, for example the Daudi line (ATCC CCL213) are preferably used.

| Mutation | Oligo oTG- | M13 M13TG | Plasmid pTG- |
|---|---|---|---|
| ABloop (404–418): 404TPAPS408 | | | |
| 404GPAPS408 | 12740 | 14017 | 14283 |
| 404TPKPS408 | 12498 | 6587 | 4289 |
| 404TPAPE408 | 12499 | 6588 | 4291 |

B. Study of the Incorporation of the Modified Fiber into the Viral Particle and of its use in the Entry of the Corresponding Adenovirus In order to be sure that the mutated viruses indeed carry the modified fiber proteins in their capsid, the viruses purified after amplification in the 293 cells are loaded onto 10% acrylamide gel under denaturing conditions (SDS-PAGE). The various proteins are detected by silver nitrate staining. Alternatively, the fiber is revealed specifically by carrying out a western blot using a serum directed against the Ad5 fiber knob (Henry et al., 1994, above). A strong signal with the expected size indicates that the viruses incorporate stoichiometric amounts of the protein of interest. Given that only the trimeric fiber is capable of binding the penton base (Novelli and Boulanger, 1991, above) and of being incorporated into the particle, the detection of the protein in the experiment above indicates that the modified fiber is still capable of forming trimers.

Use of the modified fiber to allow the entry of the corresponding mutated virus can be studied by carrying out the competition experiments using recombinant knob as described above in Example 1B. An efficient infection in the presence of saturating concentrations of the wild-type peptide indicates an infection independent of the binding to the natural primary receptors. This suggests a greatly decreased affinity of the modified fiber for its receptors.

EXAMPLE 6

Insertion of the Ligand Into a Capsid Protein Other Than the Fiber, in Combination with one of the Abovementioned Modifications of the Fiber This example describes the insertion of the EGF ligand into the hexon capsid protein. Of course, it is preferable for the corresponding adenovirus to have lost its ability to attach to the natural cellular receptor. Its genome can, for example, include a modified fiber gene, or lack a portion, at least, of the fiber sequences.

A transfer plasmid for the homologous recombination covering the region of the Ad5 genome encoding the hexon (nt 18842–21700) is constructed. The HindIII-XhoI fragment of Ad5 (nt 18836–24816) is cloned into pBSK+ (Stratagene) digested with these same enzymes, to give the plasmid pTG4224. The sequences encoding the EGF peptide are introduced into the L1 hypervariable loop of the hexon by creating chimeric fragments using PCR: hexon (nt19043–19647)-XbaI-EGF-BsrGI-hexon (nt19699–20312). The nt19043 to 19647 fragment is obtained by PCR amplification using the plasmid pTG3602 with the oligonucleotides oTG11102 (SEQ ID NO: 17) and oTG11103 (SEQ ID NO: 18). The ntl9699 to 20312 fragment is amplified from the same DNA with the oligonucleotides oTG11104 (SEQ ID NO: 19) and oTG11105 (SEQ ID NO: 20). The EGF is cloned using the cDNA with the aid of the oligonucleotides oTG11106 (SEQ ID NO: 21) and oTG11107 (SEQ ID NO: 22) allowing the EGF coding sequence to be placed in frame with the hexon. The PCR products are digested with the appropriate enzymes and then religated. The chimeric fragment can then be inserted by homologous recombination into the plasmid pTG4224 linearized with NdeI (nt 19549), to give pTG4229. The sequences encoding the modified hexon can be obtained by HindIII-XhoI digestion and repositioned in their genomic context by homologous recombination. Use may be made of the vector pTG3602, pTG4607 or pTG4629 linearized with SgfI, or a vector carrying the adenoviral genome deleted of the fiber sequences (such as pTG4607 described above) or expressing a modified fiber.

The adenoviral genome incapable of producing a functional native fiber is obtained through a deletion which affects the initiator codon, but which does not extend to the other adenoviral ORFs. The following is carried out: the adenoviral fragment 5' of the deletion (nt 30564 to 31041) is amplified by PCR using the primers oTG7171 and oTG7275 (SEQ ID NO: 23 and 24). The amplification of the fragment positioned 3' (nt 31129 to 33099) uses the primers oTG7276 and oTG7049 (SEQ ID NO: 25 and 26). The PCR fragments are digested with XhoI and ligated before being introduced by homologous recombination into the vector pTG6591 linearized with NdeI, to give pTG4602. Then, the BstEII fragment isolated from the latter is subjected to homologous recombination with the vector pTG3602 digested with SpeI. pTG4607 is obtained. The vector pTG4629 is equivalent to pTG4607, but also carries the LacZ expression cassette in place of E1.

The corresponding viruses can be obtained after transfecting 293 cells or 293 cells expressing the wild-type fiber (Legrand et al., 1999, above), or cells overexpressing the receptor for EGF. The study of the specificity of infection may be carried out as described previously, using EGF as a competitor.

What is claimed is:

1. An isolated modified fiber of an adenovirus, comprising at least one mutation at one or more residues within the region of said fiber stretching from beta sheet A to beta sheet B, and including loop AB, wherein said isolated fiber is of type 5 adenovirus and comprises the substitution of the serine at position 408 of SEQ ID NO: 1 with an aspartic acid.

2. Adenoviral particle which lacks a functional native fiber, and comprises a fiber according to claim 1.

3. Adenoviral particle according to claim 2 which is empty.

4. Adenoviral particle according to claim 2, which contains an adenoviral genome.

5. Adenoviral particle according to claim 4, wherein said adenoviral genome is a replication-defective recombinant adenoviral genome.

* * * * *